United States Patent [19]

Rossmoore

[11] Patent Number: 4,708,808

[45] Date of Patent: Nov. 24, 1987

[54] SYNERGISTIC ANTIMICROBIAL OR BIOCIDAL MIXTURES

[75] Inventor: Harold W. Rossmoore, Oak Park, Mich.

[73] Assignee: The Board of Governors of Wayne State University, Detroit, Mich.

[21] Appl. No.: 28,460

[22] Filed: Mar. 20, 1987

Related U.S. Application Data

[62] Division of Ser. No. 728,793, Apr. 30, 1985, Pat. No. 4,666,616.

[51] Int. Cl.⁴ ............... C10M 129/00; C10M 139/00
[52] U.S. Cl. ............................. 252/11; 252/51.5 R; 252/35; 252/42.7; 252/49.3; 252/49.5
[58] Field of Search ............... 252/11, 35, 49.3, 49.5, 252/42.7, 51.5 R

[56] References Cited

U.S. PATENT DOCUMENTS

| | | | |
|---|---|---|---|
| 4,101,433 | 7/1978 | Purcell et al. | 252/49.5 |
| 4,107,060 | 8/1978 | Schick et al. | 252/49.5 |
| 4,129,589 | 12/1978 | Shringarpurey et al. | 252/49.5 |
| 4,180,473 | 12/1978 | Maurer et al. | 252/49.5 |
| 4,279,762 | 7/1981 | Lewis et al. | 252/49.5 |

Primary Examiner—Jacqueline V. Howard
Attorney, Agent, or Firm—Ian C. McLeod

[57] ABSTRACT

Synergistic anti-microbial compositions containing a mixture of a metal complex of a polyfunctional organic ligand and a biocidal composition which contains or releases a lower aldehyde containing 1 to 5 carbon atoms are described. The compositions are particularly useful as metal working fluids at alkaline pH and have a broad spectrum of activity against fungi and bacteria.

11 Claims, No Drawings

SYNERGISTIC ANTIMICROBIAL OR BIOCIDAL MIXTURES

This application is a division of application Ser. No. 728,793, filed 4-30-85, now U.S. Pat. No. 4,666,616.

BACKGROUND OF THE INVENTION

1. Field of the Invention

The present invention relates to synergistic antimicrobial or biocidal compositions including in admixture a metal complex of a polyfunctional organic ligand and a biocidal composition which contains or releases a lower aldehyde having 1 to 5 carbon atoms and having a broad spectrum of biocidal activity against both bacteria and fungi. In particular the present invention relates to the use of monocopper (II) disodium citrate as the complex and 1,3,5-tris substituted hexahydro-s-triazine as the biocide in such compositions.

2. Prior Art

The prior art has described metal salts (metal ions) metal complexes of organic ligands as antimicrobial or biocidal compounds. U.S. Pat. Nos. 4,055,655 to Maurer et al 4,129,589 to Shringarpurey et al and 4,180,473 to Maurer et al particularly describe ligands. The process for the manufacture of the ligands is described in U.S. Pat. No. 4,278,610 to Maurer et al. The problem is that these compounds are relatively poor antimicrobials in relation to both fungi and bacteria and even large amounts provide protection for only a limited period of time. They have very limited effectiveness against fungi.

Disodium monocopper (II) citrate (MCC) is particularly described an an antimicrobial compound in U.S. Pat. No. 4,055,655 to Maurer et al. Metalworking fluid (MWF) stabilizing activity is particularly described in U.S. Pat. No. 4,129,509 to Shringarpurey et al. This latter patent states that the compound is effective against microorganisms growing in alkaline environments (pH 8–12) due to the stability of the metal complex ligand at high pH, with dissociation into toxic copper ions occurring upon encountering the lower pH (7.0) within microbial cells. Most fungi are not significantly inhibited by MCC. Studies on MCC have shown that it can temporarily inhibit the growth of *Pseudomonas aeruginosa* in laboratory media and transiently reduce the cell count in MWF contaminated with Pseudomonas spp. The use of MCC as a MWF additive is becoming more widespread and an improvement in its effectiveness was needed.

Although bacteria are highly important in the biodeterioration of MWF, fungi and yeast can play a major role as well, especially in the synthetic fluids (Bennett, E. O., "The Deterioration of Metal Working Fluids," Prog. Indust. Microbiol., 13, p 121 (1974)), (Rossmoore, H. W. and Holtzman, G. H., "Growth of Fungi in Cutting Fluids," Dev. Indust. Microbiol., 15, pp 273–280 (1974)). Fusarium and Cephalosporium are prominent fungal contaminants, and among the yeasts, Candida and Trichosporon spp. are often isolated.

Fungi and yeast are known to be sensitive to the toxic effects of Copper ion (Hugo, W. B. and Russell, A. D., "Types of Antimicrobial Agents," in: Principles and Practices of Disinfection, Preservation and Sterilization, Russell, A. D., W. B. Hugo, and G. A. J. Ayliffe (Eds.), Blackwell Scientific Publications, Boston, p. 69 (1982)) and consequently the effect of MCC at high pH on a representative yeast, *Candida tropicalis*, was studied. It was found that as a result of the machining operation itself, MWF can become contaminated with selectively large concentrations of soluble iron. The high stability constant of ferric citrate can allow exchange reactions between the ferric and copper ions in binding to the citrate ligand (Ashcroft, S. J. and Mortimer, C. T., Thermochemistry of Transition Metal Complexes, Academic Press, New York (1970)). Such reactions destroy the antimicrobial activity of MCC in alkaline environments.

There are numerous biocides which contain or release an aldehyde in situ and such biocides may not be generally recognized as functioning by releasing an aldehyde. Usually an aldehyde is used in the preparation of these biocides. A simple test for the presence of an aldehyde in situ is hydrolysis and then dimethone reaction which forms a precipitate with the aldehyde (Pasto, D. J. and C. R. Johnson, Organic Structure Determination, Prentice Hall, Inc. New Jersey (1969)). Usually these biocides do not show broad spectrum acitivity against fungi and bacteria.

OBJECTS

It is therefore an object of the present invention to provide synergistic antimicrobial or biocidal compositions which are mixtures of an aldehyde containing or releasing composition and a heavy metal complex of a polyfunctionaly organic ligand which contain less than a minimum fungicidally and bacteriocidally effective dosage of the biocide alone. It is also an object of the present invention to provide a method for the use of such synergistic compositions. These and other objects will become increasingly apparent by reference to the following description.

GENERAL DESCRIPTION

The present invention relates to a concentrated composition which comprises in admixture a metal ion (A); and a biocide (B) which contains or releases a lower aldehyde having 1 to 5 carbon atoms in an aqueous solution, wherein the biocide (B) is present in an amount with the metal ion (A) which is less than is required for suppressing fungal and bacterial activity alone when the composition is introduced into a fluid which contains both the fungi and the bacteria. Preferably the metal ion is part of a complex of a polyfunctional organic ligand.

Also the present invention relates to a biocidal metal working composition which comprises in admixture: a metal working fluid in admixture with a biocidal amount of a metal complex of a polyfunctional ligand (A) and a biocide (B) which contains or releases a lower aldehyde having 1 to 5 carbon atoms in an aqueous solution, wherein the biocide (B) is present in an amount with the metal complex (A) which is less than is required for suppressing fungal and bacterial acitivity alone in the fluid when the fluid contains both the fungi and the bacteria.

Further the present invention relates to a method for producing a fluid having biocidal activity wherein the fluid supports microbial growth which comprises: providing a biocidal amount of a metal ion (A) and a biocide (B) which contains or releases an aldehyde having 1 to 5 carbon atoms in the fluid, wherein the biocide (B) is present in an amount which is less than is required for fungal and bacterial activity alone in the fluid when the fluid contains both the bacteria and the fungi.

In particular the present invention relates to a preferred concentrated composition which comprises in admixture: a metal complex consisting essentially of disodium monocopper (II) citrate; and a biocide selected from the group consisting of a lower aldehyde containing 1 to 5 carbon atoms; 1,3,5-tris(2-hydroxyethyl)hexahydro-s-triazine; oxazolidines; n-methylolchloroacetamide; 1,3,5-tris(ethyl)hexahydro-s-triazine; 4,4'(2-ethyl-2-nitrotrimethylene)dimorpholine; 4-(2-nitrobutyl)morpholine; tris(hydroxymethyl)nitromethane; 6-acetoxy-2,4-dimethyl-m-dioxane; 1-(3-chloroallyl)-3,4,7-triaza-1-azoniaadamantane chloride and wherein the biocide is present in an amount with the metal complex which is less than is required for suppressing fungal and bacterial activity when the concentrated composition is introduced into a fluid which suppresses fungal and bacterial growth when the fluid contains both the fungi and the bacteria.

The present invention further relates to a preferred method for producing a fluid having biocidal activity which comprises: providing a biocidal amount of a metal complex consisting essentially of disodium monocopper (II) citrate and a biocide selected from the group consisting of a lower aldehyde containing 1 to 5 carbon atoms; 1,3,5-tris(2-hydroxyethyl)hexahydro-s-triazine; oxazolidines; n-methylolchloroacetamide; 1,3,5-tris(ethyl)hexahydro-s-triazine; 4,4'(2-ethyl-2-nitrotrimethylene)dimorpholine; 4-(2-nitrobutyl)morpholine; tris(hydroxymethyl)nitromethane; 6-acetoxy-2,4-dimethyl-m-dioxane; 1-(3-chloroallyl)-3,4,7-triaza-1-azoniaadamantane chloride and wherein the biocide is present in an amount with the metal complex which is less than is required for suppressing fungal and bacterial activity when the concentrated composition is introduced into a fluid which suppresses fungal and bacterial growth when the fluid contains both the fungi and the bacteria.

Finally the present invention relates to a biocidal metal working composition which comprises in admixture: a metal working fluid in admixture with a biocidal amount of a metal complex consisting essentially of disodium monocopper (II) citrate and a biocide selected from the group consisting of a lower aldehyde containing 1 to 5 carbon atoms; 1,3,5-tris(2-hydroxyethyl)hexahydro-s-triazine; oxazolidines; n-methylolchloroacetamide; 1,3,5-tris(ethyl)hexahydro-s-triazine; 4,4'(2-ethyl-2-nitrotrimethylene)dimorpholine; 4-(2-nitrobutyl)morpholine; tris(hydroxymethyl)nitromethane; 6-acetoxy-2,4-dimethyl-m-dioxane; 1-(3-chloroallyl)-3,4,7-triaza-1-azoniaadamantane chloride, wherein the biocide is present in an amount which is less than is required for suppressing fungal and bacterial activity alone in the fluid when the fluid contains the bacteria and the fungi. Preferably the biocide is a triazine, or oxazolidines.

Preferably the metal complex of the liquid of the ligand is present in an amount between about 50 and 250 ppm as the metal derived from the complex. An amount of 50 to 100 ppm is particularly preferred. The biocide which contains or releases the aldehyde is present in an amount between about 50 ppm and 2000 ppm, the amount depending upon the aldehyde released or present in the fluid. Preferably 50 to 400 ppm is used. Most preferred is 200 to 400 ppm. A molar ratio of aldehyde to metal ion of about 1 to 3 and 3 to 1 is preferred.

SPECIFIC DESCRIPTION

The cultures of the fungi and the bacteria used were grown separately and then added to the metal working fluid (MWF). The strains were those isolated from spoiled MWF. The fungi were grown on Sabouraud dextrose agar, removed and then suspended in growth medium at $10^5$ to $10^6$ CFU per ml at 25° C. The bacterium were grown in soy, protein, casein digest medium (Difco Detroit, Mich.) to $10^9$ cells per ml at 25° C.

The method for screening potential biocides in MWF has been previously described by Rossmoore, et al in Lubr Eng 35 (10) 559–563 (1979). Ninety (90) ml of a 5% oil-in-water emulsion was added to each test system in a 180 ml screw cap prescription bottle. Each bottle subsequently was challenged with 5 ml of the mixed bacterial inoculum and 5 ml of the mixed fungal inoculum grown as previously described, both derived from spoiled, contaminated MWF. Biocides and MCC at indicated levels (Tables 1 and 2) were added to each bottle with appropriate controls. Samples were incubated at room temperature with shaking for 72 hours.

RESULTS AND DISCUSSION

The activity of MCC against the mixtures of the fungi and the bacteria is shown in Tables 1 and 2. The compound has limited effectiveness at alkaline pH but this effectiveness is of a temporary nature as shown by Piet and Rossmoore Lubr. Eng. 41(2) 103–105 (1985). The results in Table 2 are in the presence of 1% by weight iron clips in the fluid which is known to inhibit MCC activity.

TABLE 1

| | | Experiment 1 | | | | |
|---|---|---|---|---|---|---|
| | | | Bacteria/ml | | Fungi/ml | |
| Compound Number | Chemical Name of Biocide | Active ppm | Without MCC | With 250 ppm MCC | Without MCC | With 250 ppm MCC |
| 1 | 1,3,5-tris (2-hydroxyethyl) hexahydro-s-triazine Recommended Effective Dosage* (RED = 1200) | 195 390 780 | $6 \times 10^7$ $<10^3$ $<10^3$ | $<10^3$ $<10^3$ $<10^3$ | $6 \times 10^4$ $1 \times 10^5$ $1 \times 10^3$ | $6 \times 10^4$ $<10^2$ $6 \times 10^2$ |
| 2 | n-methylolchloroacetamide (RED = 900 ppm) | 98 195 390 | $3 \times 10^7$ $1 \times 10^7$ $8 \times 10^7$ | $4 \times 10^7$ $7 \times 10^5$ $<10^3$ | $2 \times 10^5$ $9 \times 10^4$ $1 \times 10^5$ | $1 \times 10^5$ $<10^2$ $7 \times 10^2$ |
| 3 | 1,3,5-tris (ethyl) hexahydro-s-triazine (RED = 950 ppm) | 95 238 475 | $6 \times 10^7$ $2 \times 10^4$ $2 \times 10^3$ | $2 \times 10^4$ $<10^3$ $<10^3$ | $8 \times 10^4$ $2 \times 10^2$ $<10^2$ | $<10^2$ $<10^2$ $<10^2$ |
| 4 | [Mixture] 4,4' (2-ethyl-2-nitrotrimethylene) dimorpholine (22.2%) + 4-(2-nitrobutyl) morpholine (77.8%) (RED = ) | 225 450 900 | $4 \times 10^7$ $1 \times 10^7$ $2 \times 10^6$ | $1 \times 10^4$ $3 \times 10^3$ $<10^3$ | $2 \times 10^5$ $1 \times 10^5$ $2.4 \times 10^4$ | $1 \times 10^5$ $2 \times 10^4$ $<10^2$ |
| 5 | tris (hydroxymethyl) nitromethane (RED = 1000 ppm) | 300 600 900 | $9 \times 10^7$ $2 \times 10^7$ $1 \times 10^6$ | $1 \times 10^6$ $<10^3$ $<10^3$ | $2 \times 10^5$ $2 \times 10^5$ $1 \times 10^5$ | $<10^2$ $<10^2$ $<10^2$ |
| 6 | 6-acetoxy-2,4-dimethyl-m- | 500 | $1 \times 10^7$ | $7 \times 10^6$ | $7 \times 10^4$ | $<10^2$ |

TABLE 1-continued

| | | | Experiment 1 | | | |
|---|---|---|---|---|---|---|
| | | | Bacteria/ml | | Fungi/ml | |
| Compound Number | Chemical Name of Biocide | Active ppm | Without MCC | With 250 ppm MCC | Without MCC | With 250 ppm MCC |
| | dioxane | 1,000 | $3 \times 10^5$ | $<10^3$ | $<10^2$ | $<10^2$ |
| | (RED = 1000 ppm) | 1,500 | $4 \times 10^6$ | $<10^3$ | $<10^2$ | $<10^2$ |
| 7 | 1-(3-chloroallyl)-3,5,7- | 68 | $10^9$ | $2 \times 10^6$ | $1 \times 10^5$ | $3 \times 10^3$ |
| | triaza-1-azonia-adamantane | 340 | $10^9$ | $2 \times 10^5$ | $1 \times 10^5$ | $2 \times 10^2$ |
| | chloride | 680 | $3 \times 10^6$ | $3 \times 10^6$ | $4 \times 10^2$ | $3 \times 10^3$ |
| | (RED = 680 ppm) | | | | | |
| — | MCC alone | 250 | $3 \times 10^7$ | | $9 \times 10^4$ | |
| — | Control | — | $4 \times 10^7$ | | $8 \times 10^4$ | |

*RED or Recommended Effective Dosage is that dosage necessary for effective suppression of bacteria or fungi $<10^2$.
MCC = monocopper citrate
Compounds 1, 2, 3, 5, and 7 are recognized formaldehyde releasers.
Compound 4 is made with formaldehyde.
Compound 6 hydrolyzes to acetaldehyde and crotonaldehyde.

TABLE 2

| | | | Experiment 2 | | | |
|---|---|---|---|---|---|---|
| | | | Bacteria/ml | | Fungi/ml | |
| Compound Number | Chemical Name of Biocide | Active ppm | Without MCC | With 250 ppm MCC | Without MCC | With 250 ppm MCC |
| 1 | 1,3,5-tris (2-hydroxyethyl) | 195 | $3 \times 10^8$ | $<10^3$ | $5 \times 10^4$ | $3 \times 10^2$ |
| | hexahydro-s-triazine | 390 | $3 \times 10^3$ | $<10^3$ | $2 \times 10^4$ | $<10^2$ |
| | Recommended Effective Dosage | 780 | $10^3$ | $<10^3$ | $<10^2$ | $<10^2$ |
| | (RED = 1200 ppm) | | | | | |
| 2 | n-methylolchloroacetamide | 98 | $5 \times 10^8$ | $1 \times 10^6$ | $1 \times 10^5$ | $<10^2$ |
| | (RED = 900 ppm) | 195 | $4 \times 10^8$ | $2 \times 10^6$ | $8 \times 10^4$ | $<10^2$ |
| | | 390 | $4 \times 10^8$ | $4 \times 10^3$ | $4 \times 10^3$ | $<10^2$ |
| 3 | [Mixture] 1,3,5-tris | 175 | $5 \times 10^7$ | $2 \times 10^4$ | $3 \times 10^4$ | $<10^2$ |
| | (2-hydroxyethyl)hexahydro-s- | 350 | $3 \times 10^3$ | $<10^3$ | $<10^2$ | $<10^2$ |
| | triazine (90%) + sodium 2- | 700 | $8 \times 10^3$ | $<10^3$ | $<10^2$ | $<10^2$ |
| | pyridinethiol-1-oxide (10%) | | | | | |
| | (RED = 700 ppm) | | | | | |
| 4 | 1-(3-chlorallyl)-3,5,7-triaza | 68 | $7 \times 10^8$ | $2 \times 19^6$ | $1 \times 10^5$ | $3 \times 10^3$ |
| | 1-azonia-adamantane chloride | 340 | $1 \times 10^9$ | $2 \times 10^5$ | $7 \times 10^4$ | $<10^2$ |
| | (RED = 680 ppm) | 680 | $3 \times 10^6$ | $3 \times 10^6$ | $4 \times 10^2$ | $3 \times 10^3$ |
| 5 | 1,3,5-tris (ethyl) hexahydro- | 238 | $6 \times 10^4$ | $4 \times 10^3$ | $<10^2$ | $<10^2$ |
| | 2-triazine | 475 | $<10^3$ | $<10^3$ | $<10^2$ | $<10^2$ |
| | (RED = 950 ppm) | 950 | $<10^3$ | $<10^3$ | $<10^2$ | $<10^2$ |
| 6 | glutaraldehyde | 115 | $1 \times 10^7$ | $4 \times 10^6$ | $1 \times 10^5$ | $<10^2$ |
| | (RED - ppm) | 230 | $1 \times 10^7$ | $2 \times 10^5$ | $1 \times 10^3$ | $2 \times 10^2$ |
| | | 345 | $5 \times 10^7$ | $5 \times 10^5$ | $1 \times 10^3$ | $<10^2$ |
| 7 | [Mixture] 4,4-dimethyloxa- | 195 | $2 \times 10^8$ | $3 \times 10^5$ | | $1 \times 10^3$ |
| | zolidine (96%) + 3,4,4-tri- | 390 | $4 \times 10^8$ | $5 \times 10^6$ | $10^5$ | $8 \times 10^4$ |
| | methyloxazolidine (4%) | 780 | $<10^3$ | $<10^3$ | $<10^2$ | $<10^2$ |
| | (RED = 1000 ppm) | | | | | |
| 8 | [Mixture] 5-hydroxymethoxy- | | | | | |
| | methyl-1-aza-3,7-dioxabicyclo | | | | | |
| | (3.3.0) octane (49%) + 5-hydroxy- | | | | | |
| | methyl-1-aza-3,7-dioxabicyclo | | | | | |
| | (3.3.0) octane (35%) + 5-hy- | | | | | |
| | droxypoly[methyleneoxy(74% $C_2$ | | | | | |
| | 21% $C_3$, 4% $C_4$, 1% $C_5$)]methyl-1- | 125 | $4 \times 10^8$ | $5 \times 10^5$ | $3 \times 10^5$ | $8 \times 10^3$ |
| | aza-3,7-dioxabicyclo(3.3.0) | 250 | $2.5 \times 10^7$ | $4 \times 10^3$ | $2 \times 10^5$ | $2 \times 10^3$ |
| | octane (16%) | 500 | $5 \times 10^6$ | $<10^3$ | $2 \times 10^5$ | $2 \times 10^3$ |
| | (RED = 1000 ppm active) | | | | | |
| — | MCC alone | 250 | $1 \times 10^7$ | | $6 \times 10^4$ | |
| — | Control | 500 | $3 \times 10^7$ | | $1 \times 10^5$ | |
| | | — | $3 \times 10^8$ | | $7 \times 10^4$ | |

MCC = monocopper citrate
Compounds 1, 2, 3, 4, and 5 and 7, 8 are recognized formaldehyde releasers.
Compound 6 contains two potential aldehyde sites.

The results in Tables 1 and 2 indicate that MCC is very effective in extending the antimicrobial activity of some of the aldehydes or aldehyde containing biocides even in the presence of ferric ion. The successes are related to the role of an aldehyde moiety in the synthesis and/or hydrolysis of the biocide. The results obtained against fungi are more striking than those found with bacteria at the dose levels used. This is an important finding since a major disadvantage of these biocides has been their inability to cost effectively control fungi and, consequently, the frequent need to use them in combination with fungicides (Rossmoore, et al. Biodeterioration of Materials 2, 286–293, 1971; DeMare, et al., Dev. Industrial Microbiol. 13, 341–346, 1972; Rossmoore, et al., 1979, cited previously). The level of MCC alone has no significant effect on either microbial population group.

Recently it has been found that resistance to a formaldehyde condensate biocide stoichiometrically confers resistance to formaldehyde itself; the converse is also true. The relationship of this resistance to formaldehyde dehydrogenase (FDH) has been reported for bacteria (Ando, et al., 1979; Kato, et al., 1983) and for yeasts (Kato, et al *Agric. Biol. Chem.* 46, 655–661, 1982). In addition, $Cu^{++}$ is reported to interfere with FDH in yeasts (Schutte, et al., *Eur. J. of Biochem* 62; 151–160, 1976).

To support the mechanism of the interaction between copper- and formaldehyde-based biocides, the following experiments were performed. *Pseudomonas aeruginosa* isolated from MWFs and maintained as a pure culture was used at a level of about 1 to $5 \times 10^7$ cells per ml. The putative molar formaldehyde equivalent of a series of the compounds listed in Tables 1 and 2 was compared to pure formaldehyde on that molar basis. (For example, 3 mM $CH_2O$ is equivalent to 1 mM 1,3,5-tris(ethyl)hexahydro-s-triazine.) Biocidal activity was found equivalent for some but not all of the formaldehyde-based biocides. This disparity could be related to the temporal and pH dependence of the hydrolytic release of formaldehyde in situ. The copper oxycitrate complex at 1 mM to 3 mM was synergistic in activity with pure formaldehyde.

At neutral pH, $Cu^{++}$ as $CuSO_4$ functions similarly to MCC as shown in Table 3.

TABLE 3

| | Changes in Cell Count (cells/ml) as a Function of Time | | | | | | |
|---|---|---|---|---|---|---|---|
| Time | Control F.A. 3 mM | F.A. 3 mM +$Cu^{++}$2 mM | F.A. 3 mM +$Cu^{++}$4 mM | F.A. 3 mM +$Cu^{++}$6 mM | $Cu^{++}$2 mM Control | $Cu^{++}$4 mM Control | $Cu^{++}$6 mM Control |
| 0 hr | $5.1 \times 10^7$ | $5.1 \times 10^7$ | $5.1 \times 10^7$ | $5.1 \times 10^7$ | $5.1 \times 10^7$ | $5.1 \times 10^7$ | $5.1 \times 10^7$ |
| 4 hr | $4.8 \times 10^4$ | $9.5 \times 10^2$ | $1 \times 10^3$ | $9.8 \times 10^2$ | $5.5 \times 10^8$ | $1.2 \times 10^8$ | $7.3 \times 10^7$ |
| 6 hr | NT | 0 | 5 | 3 | | | |
| 8 hr | $5.3 \times 10^3$ | 0 | 0 | 0 | | | |
| 16 hr | $1.1 \times 10^3$ | 0 | 0 | 0 | | | |
| 22 hr | $4.7 \times 10^4$ | 0 | 0 | 0 | | | |
| 30 hr | $8.3 \times 10^7$ | 0 | 0 | 0 | | | |

*pH = 7.0
3 mM F.A. = 90 ppm
2 mM $CuSO_4$ - 127.09 ppm copper
4 mM $CuSO_4$ = 245.18 ppm copper
6 mM $CuSO_4$ = 381.27 ppm copper Table 3 shows the synergistic effect of copper sulfate on formaldehyde (FiA) biocidal activity against *Pseudomonas aeruginosa* in trypticase soy broth. At 1 mM formaldehyde there was a decrease in growth for a limited period of time. At the pH of MWFs (about 8.0 to 9.5), $CuSO_4$ precipitates as $Cu(OH)$, and $Cu^{++}$ is not available. This result appears to reinforce the role of $Cu^{++}$ in the inactivation of FDH. Since $Cu^{++}$ ordinarily is precipitated as the insoluble $Cu(OH)_2$ at the pH of MWF, the use of MCC in MWF is a novel and effective way to deliver $Cu^{++}$ to suitable molecular sites in the microbial cell.

It is intended that the foregoing description be only illustrative of the present invention and that the present invention be limited only by the hereinafter appended claims.

I claim:

1. A concentrated composition which comprises in admixture:
   (a) a heavy metal ion (A) in an amount between about 50 and 250 ppm; and
   (b) a biocide (B) which contains or releases a lower aldehyde containing 1 to 5 carbon atoms in an aqueous solution wherein the biocide is tris-(hydroxymethyl)nitromethane, wherein the heavy metal ion with the biocide is toxic to fungal and bacterial growth, wherein the biocide (B) is present in an amount with the metal ion (A) which is less than is required for suppressing fungal and bacterial activity alone when the composition is introduced into a fluid which contains both the fungi and bacteria and wherein the fungal and bacterial growth is suppressed for 72 hours in the presence of 1% by weight iron chips in the solution.

2. The biocidal composition of claim 1 wherein the concentration of (B) is between from about 50 ppm to about 2000 ppm.

3. The biocidal composition of claim 1 wherein in (A) a citrate is a ligand with the metal ion and the metal ion is copper.

4. A biocidal metal working composition which comprises in admixture:
   (a) a metal working fluid in admixture with a biocidal amount of
   (b) a heavy metal complex of a polyfunctional ligand (A) and a biocide (B) which contains or releases a lower aldehyde containing 1 to 5 carbon atoms in an aqueous solution, wherein the biocide is tris-(hydroxymethyl)nitromethane, wherein the metal complex releases a metal ion in the fluid which is toxic to fungal and bacterial growth and wherein the metal ion is provided in the fluid in an amount between 50 and 250 ppm, wherein the biocide (B) is present in an amount with the metal complex (A) which is less than is required for suppressing fungal and bacterial activity alone in the fluid when the fluid contains both the fungi and bacteria and wherein fungal and bacterial growth is suppressed for 72 hours in the presence of 1% by weight of iron chips in the solution.

5. The biocidal composition of claim 4 wherein the concentration of (B) is between from about 50 ppm to about 2000 ppm and the fluid is alkaline.

6. The biocidal composition of claim 4 wherein the composition contains more than 50 ppm of the metal ion from (A).

7. The biocidal composition of claim 5 wherein in A a citrate is the ligand and the metal is copper.

8. A method for producing a fluid having biocidal activity wherein the fluid supports microbial growth which comprises:
   providing a biocidal amount of a metal ion (A) and a biocide (B) which contains or releases an aldehyde containing 1 to 5 carbon atoms in the fluid, wherein the biocide is tris-(hydroxymethyl)nitromethane, wherein the metal ion with the biocide is toxic to fungal and bacterial growth and wherein the metal ion is provided in the fluid in an amount between 50 and 250 ppm, wherein the biocide (B) is present in an amount which is less than is required for suppressing bacterial and fungal activity alone in the fluid when the fluid contains both the bacteria and the fungi and wherein the fungal and bacterial growth is suppressed for 72 hours in the presence of 1% by weight iron chips in the fluid.

9. The biocidal composition of claim 8 wherein the concentration of (B) is between from about 50 ppm to about 2000 ppm.

10. The method of claim 8 wherein the composition contains more than 50 ppm of metal ion from (A).

11. The method of claim 8 wherein in (A) a citrate is a ligand with the metal ion and the metal ion is copper.

* * * * *